United States Patent [19]
Colella et al.

[11] 3,943,254
[45] Mar. 9, 1976

[54] BETA-ADRENERGIC ANTAGONISTS

[75] Inventors: Donald F. Colella, West Norriton, Pa.; Carl Kaiser, Haddon Heights, N.J.

[73] Assignee: Smithkline Corporation, Philadelphia, Pa.

[22] Filed: Nov. 7, 1974

[21] Appl. No.: 521,597

Related U.S. Application Data

[62] Division of Ser. No. 389,772, Aug. 20, 1973, Pat. No. 3,860,647.

[52] U.S. Cl. ............................................... 424/321
[51] Int. Cl.² .................................... A61K 31/165
[58] Field of Search .................................. 424/321

[56] References Cited

UNITED STATES PATENTS

| | | | |
|---|---|---|---|
| 3,478,149 | 11/1969 | Larsen et al. | 424/321 |
| 3,701,808 | 10/1972 | Hartley et al. | 424/321 |
| 3,758,692 | 9/1973 | Larsen et al. | 424/321 |

*Primary Examiner*—Norman A. Drezin
*Attorney, Agent, or Firm*—Stuart R. Suter; Alan D. Lourie; William H. Edgerton

[57] ABSTRACT

α-Aminomethyl-4-hydroxy-3-sulfamylbenzyl alcohols and 4-hydroxy-3-sulfamylphenethylamines are disclosed. These compounds have β-adrenergic antagonist activity.

7 Claims, No Drawings

BETA-ADRENERGIC ANTAGONISTS

This is a division of application No. 389,772 filed Aug. 20, 1973, now U.S. Pat. No. 3,860,647.

This invention relates to substituted α-aminomethylbenzyl alcohols and phenethylamines which have β-antagonist activity.

The compounds of the invention are represented by the following structural formula:

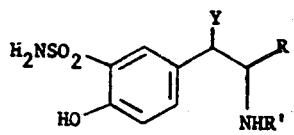

where
R is hydrogen or alkyl of $C_1$–$C_4$;
R' is alkyl of $C_1$–$C_6$, cycloalkyl of $C_3$–$C_6$, $XC_6H_4(CH_2)_2CH(CH_3)$, $XC_6H_4(CH_2)_2C(CH_3)_2$, $XC_6H_4CH_2CH(CH_3)$, or $XC_6H_4CH_2C(CH_3)_2$;
Y is hydrogen or hydroxy; and
X is hydrogen, hydroxy, or methoxy.

Preferred compounds are those where R is hydrogen. Also, preferred are compounds where R' is isopropyl, t-butyl, cyclohexyl, 4-phenyl-2-butyl, 3-phenyl-2-methyl-2-propyl, 4-phenyl-2-methyl-2-butyl, 3-phenyl-2-propyl, or 4-(p-hydroxyphenyl)-2-methyl-2-butyl.

The compounds of this invention may be used in the form of a pharmaceutically acceptable acid addition salt which is also within the scope of this invention. Such salts, prepared by well known methods, are formed from both inorganic and organic acids such as maleic, fumaric, benzoic, ascorbic, pamoic, succinic, bismethylenesalicyclic, methanesulfonic, ethanedisulfonic, acetic, oxalic, propanoic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric, and nitric acids.

A general method of preparation of the compounds where Y is hydroxy is shown in Scheme I.

SCHEME I

The aniline compound (I) is treated with nitrous acid followed by sulfur dioxide and cupric chloride to give compound II. Reaction of II with ammonia gives the sulfamyl derivative which is brominated to give the bromo ketone III. Nucleophilic displacement of the bromine with an appropriate secondary benzylamine gives compound IV. Debenzylation and reduction of the ketone are effected by catalytic hydrogenation.

Compounds where Y is hydrogen are prepared by reduction of the benzyl alcohols (V); for example, with diborane.

The aminobenzyloxyphenones used as starting materials herein are known or are prepared by methods known in the art. For example, a 4-hydroxyphenone is nitrated with nitric acid at −20° to −30°C. to yield the 4-hydroxy-3-nitrophenone which is reacted with benzyl chloride in the presence of potassium hydroxide or potassium carbonate to give the 4-benzyloxy-3-nitrophenone and the latter is reduced to the 3-amino-4-benzyloxyphenone using Raney nickel and hydrazine hydrate, platinum oxide and hydrogen or sodium sulfhydrate ($NaSH.2H_2O$) in dimethylformamide.

When Y is hydroxy an asymmetric carbon is present and D or L optical isomers may be present. In addition, two asymmetric carbon atoms are present when Y is hydroxy and R is not hydrogen; therefore, erythro and threo diastereomers may be present. The resolution of the optical isomers may be done by standard methods. It is to be understood that all isomers, whether separated or in mixtures, are within the scope of this invention.

The compounds of this invention may be administered orally or parenterally in conventional dosage unit forms such as tablets, capsules, injectables or the like, by incorporating the appropriate dose of the compound with carriers according to accepted pharmaceutical practices. Preferably a compound or an acid addition salt thereof is administered orally to an animal organism in a tablet or capsule comprising an amount sufficient to produce β-adrenergic antagonist activity. Each dosage unit will contain the active medicament in an amount of about 20 mg to about 300 mg, preferably about 25 mg to about 200 mg. Advantageously equal doses will be administered 2 to 4 times daily with the daily dosage regimen being about 40 mg to about 1200 mg, preferably about 50 mg to about 800 mg.

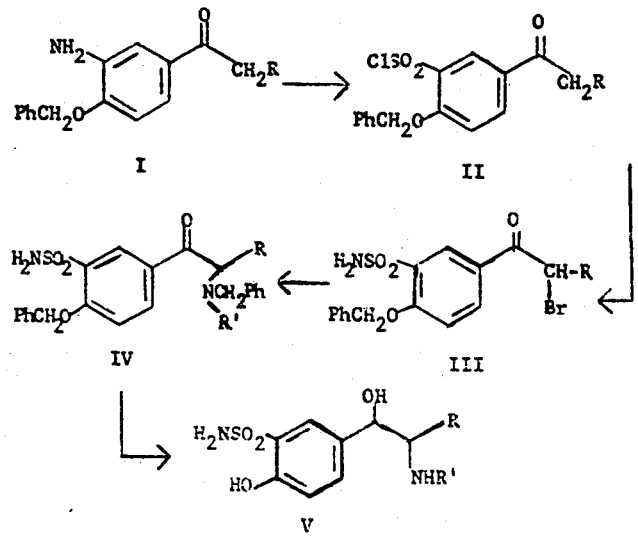

The pharmaceutical carrier employed may be, for example, either a solid or liquid. Exemplary of solid carriers are lactose, terra laba, sucrose, talc, gelatin, agar, pectin, acacia, magnesium stearate, stearic acid and the like. Exemplary of liquid carriers are syrup, peanut oil, olive oil, water and the like. Similarly the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form, or in the form of a troche or lozenge. The amount of solid carrier will vary widely but preferably will be about 25 mg to about 1 g. If a liquid carrier is used, the preparation will be in the form of a syrup, emulsion, soft gelatin capsule, sterile injectable liquid such as an ampule, or an aqueous or nonaqueous liquid suspension.

The compounds of this invention block β-adrenergic receptors and thus have use in the treatment or prophylaxis of cardiovascular disorders; for example, arrythmia, angina pectoris, and hypertension.

A preferred compound of this invention is 4-hydroxy-α-isopropylaminomethyl-3-sulfamylbenzyl alcohol which displayed β-antagonist activity in anesthetized dogs. For instance, the compound at 10 mg/kg (base-)i.v. showed competitive inhibition of diastolic blood pressure decreases and heart rate increases due to i.v. challenges of increasing amounts of isoproternol before and after administration of 4-hydroxy-α-isopropylaminomethyl-3-sulfamylbenzyl alcohol.

The following examples illustrate the invention but are not to be construed as limiting the scope thereof.

EXAMPLE 1

A solution of 4-benzyloxy-3-aminoacetophenone (4.8 g, 0.02 mol) in concentrated HCl (10 ml) and glacial acetic acid (10 ml) was cooled to 0°–10° and stirred while an aqueous solution of $NaNO_2$ (2.0 g) was added dropwise. After the solution was stirred 15 minutes, a 30% $SO_2$ in glacial acetic acid solution (20 g) and $CuCl_2.2H_2O$ (1.0 g) were added in portions. The solid product, 4-benzyloxy-3-chlorosulfonylacetophenone, was collected and recrystallized from ethyl acetate; mp 154°–155.5°C.

EXAMPLE 2

A suspension of 4-benzyloxy-3-chlorosulfonylacetophenone (15.4 g) in dioxane (102 ml) was warmed to effect complete solution and then was stirred with concentrated aqueous ammonia (60 ml) for 20 minutes at room temperature. The solution was cooled in an icebath and the 4-benzyloxy-3-sulfamylacetophenone was collected, mp 183°–4°C.

EXAMPLE 3

To a stirred suspension of 4-benzyloxy-3-sulfamylacetophenone (3.05 g, 0.01 mol) and benzoyl peroxide (0.2 g) in chloroform (100 ml) was added a solution of bromine (1.6 g, 0.01 mol) in chloroform (10 ml). The reaction was irradiated with a sun lamp for 30 minutes during which time the bromine color disappeared. The solution was cooled and the 4-benzyloxy-α-bromo-3-sulfamylacetophenone was collected and recrystallized from ethanol, mp 163°–5°C.

EXAMPLE 4

Isopropylbenzylamine (0.78 g, 5.2 mmol) in acetonitrile (4 ml) was added to a solution of 4-benzyloxy-α-bromo-3-sulfamylacetophenone (1.0 g, 2.6 mmol) in acetonitrile (20 ml). The solution was stirred at room temperature for 3 hours, diluted with ether (100 ml), and filtered. The filtrate was acidified with ethereal HCl to give a gum which was triturated with acetone to produce solid 4-benzyl-α-isopropylbenzylamino-3-sulfamylacetophenone hydrochloride which was recrystallized from methanol-ether; mp 182°–183.5°C.

The hydrochloride salt (2.95 g, 6 mmol) was dissolved in methanol (100 ml) and hydrogenated at 50 psi for 1.75 hours over 10% Pd on carbon (1.0 g) which was wetted with water. The reaction mixture was filtered and concentrated, the residue was mixed with toluene and evaporated to give 4-hydroxy-α-isopropylaminomethyl-3-sulfamylbenzyl alcohol hydrochloride, mp 183°–4°C.

EXAMPLE 5

When t-butylbenzylamine, cyclohexylbenzylamine, (4-phenyl-2-butyl)benzylamine, (4-phenyl-2-methyl-2-butyl)benzylamine,(3-phenyl-2-propyl)benzylamine, (3-phenyl-2-methyl-2-propyl)benzylamine, and [4-(p-hydroxyphenyl)-2-methyl-2-butyl]benzylamine are substituted in the procedure of Example 4 for isopropylbenzylamine the following compounds are obtained:

α-t-butylaminomethyl-4-hydroxy-3-sulfamylbenzyl alcohol

α-cyclohexylaminomethyl-4-hydroxy-3-sulfamylbenzyl alcohol 4-hydroxy-α-(4-phenyl-2-butyl)aminomethyl-3-sulfamylbenzyl alcohol 4-hydroxy-α-(4-phenyl-2-methyl-2-butyl)aminomethyl-3-sulfamylbenzyl alcohol 4-hydroxy-α-(3-phenyl-2-propyl)aminomethyl-3-sulfamylbenzyl alcohol 4-hydroxy-α-(3-phenyl-2-methyl-2-propyl)aminomethyl-3-sulfamylbenzyl alcohol 4-hydroxy-α-[4-(p-hydroxyphenyl)-2-methyl-2-butyl]aminomethyl-3-sulfamylbenzyl alcohol

EXAMPLE 6

When 3-amino-4-benzyloxypropophenone or 3-amino-4-benzyloxybutyrophenone are substituted for 3-amino-4-benzyloxyacetophenone in the procedure of Example 1 and the products obtained carried through the procedures of Examples 2, 3, and 4 one obtains 4-hydroxy-α-(1-isopropylaminoethyl)-3-sulfamylbenzyl alcohol and 4-hydroxy-α-(1-isopropylaminopropyl)-3-sulfamylbenzyl alcohol. Reduction of these benzyl alcohols with diborane as in Example 7 gives 4-hydroxy-α-methyl-3-sulfamylphenethylamine and 4-hydroxy-α-methyl-3-sulfamylphenethylamine.

EXAMPLE 7

4-Hydroxy-α-isopropylaminomethyl-3-sulfamylbenzyl alcohol (2.74 g) is obtained from the hydrochloride salt in Example 4 and refluxed with 150 ml of 1.6M diborane in THF for 2 days. The solvent is evaporated and the residue is stirred with methanol and evaporated several times. The product is taken up in ethanol and acidified with ethereal HCl; N-isopropyl-4-hydroxy-3-sulfamylphenethylamine hydrochloride is obtained.

By similar procedures the benzyl alcohols of Example 4 and 5 are reduced to the corresponding phenethylamines.

EXAMPLE 8

| Ingredients | Mg./Tablet |
|---|---|
| 4-hydroxy-α-isopropylaminomethyl-3-sulfamyl-benzyl alcohol | 50 |
| Calcium sulfate, dihydrate | 125 |
| Sucrose | 25 |
| Starch | 15 |
| Talc | 5 |
| Stearic acid | 3 |

The sucrose, calcium sulfate and active medicament (as the hydrochloride) are thoroughly mixed and granulated with hot 10% gelatin solution. The wetted mass is passed through a No. 6 mesh screen directly onto drying trays. The granules are dried at 120°F. and passed through a No. 20 mesh screen, mixed with the starch, talc and stearic acid, and compressed into tablets.

We claim:

1. A pharmaceutical composition having β-adrenergic antagonist activity comprising an amount sufficient to produce β-adrenergic antagonist activity of a compound of the formula

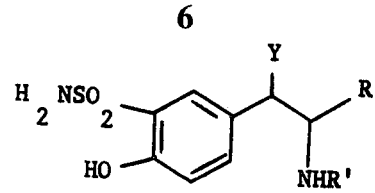

R is hydrogen or alkyl of $C_1$–$C_4$;
R' is alkyl of $C_1$–$C_6$, cycloalkyl of $C_3$–$C_6$, $XC_6H_4(CH_2)_2CH(CH_3)$, $XC_6H_4(CH_2)_2C(CH_3)_2$, $XC_6H_4CH_2C(CH_3)_2$, or $XC_6H_4CH_2CH(CH_3)$;
X is hydrogen, hydroxy, or methoxy; and
Y is hydrogen or hydroxy
or a nontoxic pharmaceutically acceptable salt thereof, and a pharmaceutical carrier therefor.

2. A pharmaceutical composition as claimed in claim 1 where R and Y are hydrogen.

3. A pharmaceutical composition as claimed in claim 1 where R is hydrogen and Y is hydroxy.

4. A pharmaceutical composition as claimed in claim 3 wherein the compound is 4-hydroxy-α-isopropylaminomethyl-3-sulfamylbenzyl alcohol.

5. A pharmaceutical composition as claimed in claim 3 wherein the compound is α-t-butylaminomethyl-4-hydroxy-3-sulfamylbenzyl alcohol.

6. A pharmaceutical composition as claimed in claim 3 wherein the compound is 4-hydroxy-α-(4-phenyl-2-methyl-2-butyl)-aminomethyl-3-sulfamylbenzyl alcohol.

7. A pharmaceutical composition as claimed in claim 2 wherein the compound is N-isopropyl-4-hydroxy-3-sulfamylphenethylamine.

* * * * *